United States Patent [19]

Bianchetti et al.

[11] 4,013,441
[45] Mar. 22, 1977

[54] HERBICIDAL COMPOSITION AND METHOD

[75] Inventors: Giuseppe Bianchetti; Donato Pocar; Riccardo Stradi, all of Milan, Italy

[73] Assignee: Societa' Italiana Resine S.I.R. S.p.A., Milan, Italy

[22] Filed: Apr. 8, 1975

[21] Appl. No.: 566,050

[30] Foreign Application Priority Data

Apr. 19, 1974 Italy .................................. 21651/74

[52] U.S. Cl. .................................. 71/92; 260/308 A
[51] Int. Cl.² .................. A01N 9/22; C07D 249/06
[58] Field of Search .................... 260/308 A; 71/92

[56] References Cited

UNITED STATES PATENTS 3,470,196  9/1969  Harvey ................................. 71/92
3,754,001  8/1973  Timmler et al. ............... 260/308 A

OTHER PUBLICATIONS

Yale, J. Med. Pharm. Chem., vol. 1, p. 121, (1959).

*Primary Examiner*—Alton D. Rollins
*Attorney, Agent, or Firm*—McNenny, Pearne, Gordon, Gail, Dickinson & Schiller

[57] ABSTRACT

A novel triazole compound of the formula:

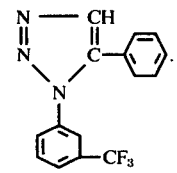

The compound is particularly effective as pre-emergency herbicide. Dosages of 2.5 Kg/Ha to 10 Kg/Ha are recommended.

8 Claims, No Drawings

HERBICIDAL COMPOSITION AND METHOD

The present invention relates to triazole compounds having herbicidal properties.

U.S. Pat. No. 3,470,196 discloses triazole compounds having herbicidal properties, of the general formula:

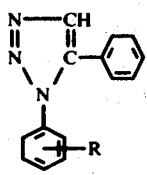

(I)

wherein R is an alkyl $C_1$-$C_4$ or —Cl, —Br or —$NO_2$.

The object of the invention is a new triazole compound, of the formula:

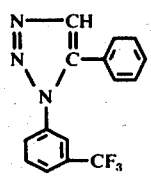

(II)

It has been found that compound (II) possesses herbicidal properties surprisingly better than those logically expectable on the basis of experiments carried out with compounds of formula (I). Compound (II) is a particularly efficient herbicide in conditions which precede the emergence of the weeds, especially so, if it is incorporated into the soil rather than simply spread on the surface of the soil. Moreover, the herbicidal action of compound (II) at dosages up to 10 Kg/Ha is selective with regard to crops such as sunflower, parsley, peas, beans, string-beans, carrots, water-melons, seed lucerne and rape, and at dosages not exceeding 2.5 Kg/Ha it is also selective with regard to beet and tomatoes. The activity of the compound (II) is particularly high upon *FESTUCA PRATENSIS, CONVOLVULUS ARVENSIS, CYNODOM DACTYLON, PHLEUM PRATENSE, BROMUS INERMIS, CHENOPODIUM ALBUM, CIRCIUM ARVENSE, DIGITARIA Sp., POA PRATENSIS, AGROSTIS TENUIS, SOLANUM Sp., NASTURTIUM SILVESTRE, SETARIA Sp., OXALIS Sp., DACTYLIS GLANERATA, FESTUCA OVINA, POA TRIVIALIS, DICHONRA REPENS, AVENA Sp., LOLIUM ITALICUM, MATRICARIA Sp., AMARANTHUS Sp., POLYGONUM Sp., CAPSELLA Sp.*

The compound of formula (II) can be prepared as follows. In a reactor of 20 liters capacity 44 g. of sodium hydroxide (1.1 moles) are dissolved at room temperature in 1.9 Kg (about 2.4 liters) of absolute ethanol. The solution is brought to about 60° C and contacted with 193 g. (1 mole) of ethyl benzoyl acetate

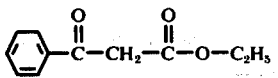

and, in 15–20 minutes, with 187 g. (1 mole) of m-trifluoromethyl-phenyl azide

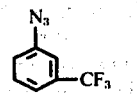

After 20–30 minutes a yellow precipitate is formed and the reaction mass solidifies.

The mass is contacted with: 270 g of sodium hydroxide (6.7 moles) dissolved in 6 liters of absolute methanol; 1158 g. of ethyl benzoyl acetate (6.0 moles) and, in 15–20 minutes, 1122 g. of m-trifluoromethyl-phenylazide (6.0 moles).

The temperature of the mass is maintained at about 60° C, and the reaction is allowed to continue for approximately one hour, whereupon the mass is cooled to 10°–15° C.

The precipitate is filtered, washed with 3 liters of absolute ethyl alcohol and is dissolved in 18 to 20 liters of hot water.

The hot aqueous solution is acidified with 5 vol.% hydrochloric acid to a pH 1–2 and subsequently cooled to 10°–15° C. The precipitate is filtered, washed several times with cold water and vacuum dried at 60°–70° C.

The result is 1550 g. of a product (yield 66–67%) with a melting point of 159°–160° C and solubility in water of 0.05% at 27° C and 0.09% at 60° C. The product has the following structural formula:

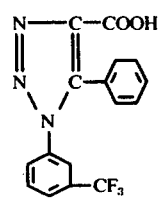

The product is then decarboxylated in a 5 liter flask immersed in an oil bath. To this end, a small proportion of the product (about 10%) is placed in the flask and is heated to the melting point, whereupon the remainder of the product is added under agitation, in such a manner that the mass always remains very fluid and so that the foaming due to the elimination of $CO_2$ is as moderate as possible.

Once the addition has been completed, the temperature of the oil bath is raised to 180° C and when $CO_2$ evolution ceases the mass is cooled to 120° C. At this point, quickly and under agitation, a quantity of ethyl alcohol double the initial quantity of the product subjected to decarboxylation is added.

The agitation is stopped and natural cooling to room temperature is allowed to proceed, whereupon the product is frozen at −10° C. The mass is filtered and the solid residue is washed with a little ethyl alcohol. The white crystals thus obtained are dried in a vacuum oven at 65° C.

Weight: 1110 g.
Yield: 85%; by concentrating the mother liquor, a further 10% of the product is recovered.

The product is insoluble in water. In absolute ethanol it dissolves to a concentration of 62% by weight at 80° C, and to 6.4% by weight at 20° C.

The product also dissolves in acetone, benzene, dioxane, methylene chloride and ethyl acetate.

For practical use, the compound (II) can be formulated in a conventional manner, in the form of solutions, suspensions, emulsions, powders or granules, according to the selected application, provided that the final herbicide product contains the compound (II) in finely dispersed form. Aqueous preparations are made by adding to the water emulsifiable or dispersable concentrates of compound (II). By means of conventional emulsifying and dispersing agents a homogeneous distribution of the compound (II) in the water is obtained. Solvents which can be used in the concentrates are acetone, cyclohexanone, benzene, toluene, xylene and chlorinated hydrocarbons. As inert fillers for powders and granules, kaolin, bentonite, diatomaceous earths and colloidal silica are recommendable. However, other inert materials normally used for such purposes may be used as well.

The preparations may contain wetting agents, emulsifiers and/or dispersing agents of the ionic or non-ionic types.

The useful doses of the compound (II) can vary from a minimum of 2kg/Ha to a maximum of 10Kg/Ha. Further information on doage is contained in the Examples hereinafter.

The compound (II) is a herbicide which interferes with the development of the weed, mainly by inhibiting the formation of the radical (root) system in such a way that after a period of time which varies with the different species, these stop growing, dry-up and die.

Thus, the best manner of using the compound (II) is in the pre-emergency period of the weeds. However, even a post-emergency treatment frequently proves effective due to high selectivity of the compound.

EXAMPLE 1

The compound (II) is formulated as a water-emulsifiable liquid by dissolving 10 g. of compound (II) in a mixture of 60 g. of xylene, 15 g. of cyclohexanone, 10 g. of Cellosolve (R.T.M.) and 5 g. of emulsifier and is used at a dose equivalent to 10Kg/Ha, on 10 trays each having a rich seed population of pisum sp., linum sp., sinapis sp., cichorium sp., beta sp., solanum sp., allium sp., avena sp., lolium sp., zea sp., respectively. In a period of 21 days in an air conditioned atmosphere all the plants growing from the seeds were destroyed, with the exception of pisum sp., and sinapis sp.

EXAMPLE 2

By operating as in example 1, but applying the compound (II) in post-emergency, that is when the small plants have reached the physiological stage of 3 actual leaves, it was observed that after 3 weeks from the treatment, the only plants still alive were pisum sp., sinapis sp., cichorium sp., and allium sp.

EXAMPLE 3

Upon sowing in seed-boxes in an air conditioned greenhouse the 18 species of plants listed hereunder, and treating in pre-emergency with 10 kg/Ha of compound (II) as in example 1, the following results were obtained:

| Botanical species: | Not treated: | Treated: |
|---|---|---|
| FESTUCA PRATENSIS | Normal growth | Inhibited germination |
| PHLEUM PRATENSE | Normal growth | Inhibited germination |
| BROMUS INERMIS | Normal growth | Inhibited germination |
| POA PRATENSIS | Normal growth | Inhibited germination |
| AGROSTIS TENUIS | Normal growth | Inhibited germination |
| DACTYLIS GLANERATA | Normal growth | Inhibited germination |
| FESTUCA OVINA | Normal growth | Inhibited germination |
| POA TRIVIALIS | Normal growth | Inhibited germination |
| DICHONDRA REPENS | Normal growth | Germinated and then necrotized |
| AVENA SATIVA | Normal growth | Abnormal development and death |
| LOLIUM ITALICUM | Normal growth | Partial inhibition of the germination, died because of lack of further growth |
| FASEOLUS VULGARIS | Normal growth | Normal growth |
| VIGNA SINENSIS | Normal growth | Normal growth |
| CUCURBITA PEPO | Normal growth | Died after germination |
| CUCUMIS MELO | Normal growth | Necrotized after germination |
| SOLANUM LYCOPERSICUM | Normal growth | Necrotized after germination |
| CICHORIUM INTYBUS | Normal growth | Necrotized after germination |
| SPINACIA OLERACEA | Normal growth | Development stopped at the level of the cotyledon leaves |

EXAMPLE 4

The results of a series of logarithmic tests in the open field for which the compound (II) was used as a 50% strength powder (obtained by finely grinding a mixture of 50% compound (II), 25% calcium carbonate powder, 20% kaolin and 5% dispersing and wetting agents) showed the limit of phyto-toxicity tolerated by the tomato and the beet to be 2.5 Kg/Ha of compound (II) and 5Kg/Ha by the oat Avena Elatior, while doses as high as 10 Kg/Ha were perfectly tolerated by the sunflower, pea, bean, stringbean, carrot, water-melon, seed lucerne and rape.

The herbicide was distributed over the ground by means of the pump "Chesterford Miniature Logarithmic Sprayer" making possible a logarithmic distribution of the product.

EXAMPLE 5

The test described in Example 4 was repeated with the difference that the herbicide was incorporated into the ground after application. The limits of selectivity with respect to crop plants were somewhat lowered but a remarkable increased phytotoxic action towards the weeds was observed.

EXAMPLE 6

A performance test in the open field on a crop of beans, treated with the compound (II) formulated as in example 4, in pre-emergency period and without incorporation into the soil, has given the following results:

perfect tolerability by the crop for all the three doses used and indicated hereunder;
good control of the weeds evaluated at
5 for a dose of 2.5 Kg/Ha
4 for a dose of 5 Kg/Ha
3 for a dose of 10 Kg/Ha.

(Method of evaluation E.W.R.C. Standard of evaluation for herbicides proposed by the European Weeds Research Council). Before the treatment was made, the following weeds were present: *Heliotropium europeanum*, Amarantus sp., *Solanum nigrum*, Euphorbia Sp., Veronica Sp., *Stellaria media*, *Convolvulus arvensis*, *Potentilla reptans*, *Sonchus asper*, Circium Sp.

EXAMPLE 7

A localized test carried out on the same ground, and in the same conditions as reported in Example 6, but on a crop of peas, confirmed both the perfect selectivity with regard to this crop too and the herbicidal action reported in the above mentioned example.

EXAMPLE 8

In a field screening test, carried out on a patch of ground which had not been cultivated for some years, but was reinstated for cultivation on the occasion of the test, an investigation was made with regard to the selectivity and the herbicidal action of the compound (11) formulated as a wettable powder of 50% strength.

This herbicide was applied at the pre-emergency stage of the crop, and also at the post-emergency stage, by means of an air pressure pump Oxford Precision Sprayer, with the following results:
a. Pre-emergency stage: 5 Kg. of compound (II)/Ha.
Selective with regard to parsley, French beans, carrots, lucerne, peas, rape.
Non-selective with regard to spinach, tomatoes, onions, beet, chicory, flax, timothy, lolium, maize.
Effectively controls *Chenopodium album*, *Circium arvense*, Digitaria sp., *Solanum nigrum*, Poa sp., *Nasturtium silvestre*, *Convolvulus arvense*, Setaria sp., oxalis sp.
Does not control: *Artemisia vulgaris*, Portulaca sp., Scirpus.
b. Pre-emergency stage: 10 Kg. compound (II)/Ha.
Selectivity: as under (a) above.
Efficiency as under (a) with the observation that those plants which escape control are nevertheless partly damaged.
c. Post-emergency stage: 5 Kg. of compound (II)/Ha.
Selectivity good for all crops, but insufficient herbicidal action on all the weeds.

We claim:
1. A triazole compound of the formula:

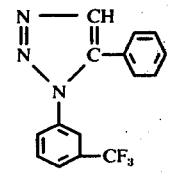

2. A herbicidal preparation comprising as active ingredient a triazole compound of the formula:

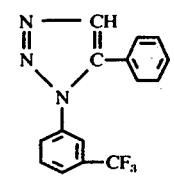

dispersed in a carrier or filler.

3. Method of controlling weeds comprising applying to the infested soil a herbicidal preparation comprising as active ingredient a triazole compound:

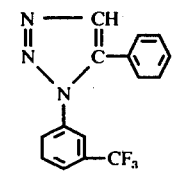

dispersed in a carrier or filler.

4. The method of claim 3, comprising applying said preparation to the infested soil in the pre-emergency stage of the weeds.

5. The method of claim 3, wherein the preparation is incorporated into the soil.

6. The method of claim 3, wherein the preparation is applied at a dosage of 2.5 Kg/Ha to 10 Kg/Ha.

7. The method of claim 4, wherein the preparation is applied at a dosage of 2.5 Kg/Ha to 10 Kg/Ha.

8. The method of claim 5, wherein the preparation is applied at a dosage of 2.5 Kg/Ha to 10 Kg/Ha.

* * * * *